United States Patent [19]

Hamanaka et al.

[11] Patent Number: 5,461,045
[45] Date of Patent: Oct. 24, 1995

[54] FUSED BENZENEOXYACETIC ACID DERIVATIVES

[75] Inventors: Nobuyuki Hamanaka; Kanji Takahashi; Hidekado Tokumoto, all of Osaka, Japan

[73] Assignee: Ono Pharmaceutical Co., Ltd., Osaka, Japan

[21] Appl. No.: 912,999

[22] Filed: Jul. 14, 1992

[51] Int. Cl.⁶ .......... A61K 31/395; A61K 31/53; C07D 211/06; C07C 205/00
[52] U.S. Cl. .......... 514/210; 514/212; 514/319; 514/345; 514/424; 514/561; 514/567; 514/569; 540/360; 540/604; 546/206; 546/216; 546/295; 546/300; 546/301; 546/302; 548/542; 548/543; 548/544; 548/556; 560/19; 560/20; 560/21; 560/22; 560/36; 560/42; 560/45; 560/47; 560/48; 560/55; 560/56; 562/435; 562/437; 562/438; 562/444; 562/452; 562/460
[58] Field of Search .......... 562/440, 460, 562/435, 437, 438, 444, 452, 460; 546/206, 216, 298, 300, 301, 302; 548/542, 543, 544, 556; 540/360, 604; 514/210, 212, 569, 314, 561, 345, 567, 424, 824, 925; 560/23, 19, 20, 21, 22, 36, 42, 45, 47, 48, 56, 55

[56] References Cited

U.S. PATENT DOCUMENTS

| 3,872,113 | 3/1975 | Fliedner | 562/440 |
| 4,278,678 | 7/1981 | Hamazaki et al. | 546/301 |
| 4,911,863 | 3/1990 | Sage et al. | 546/301 |

FOREIGN PATENT DOCUMENTS

| 0013607 | 7/1980 | European Pat. Off. |
| 0043292 | 1/1982 | European Pat. Off. |
| 0270929 | 6/1988 | European Pat. Off. |
| 3504677 | 8/1986 | Germany . |

OTHER PUBLICATIONS

Chemical Abstract, vol. 81, #77733w Cragoe et al., 1974, "2,2-Disubstituted 1-oxo-5-indanyloxy-(or-thio)alkanecarboxylic acids".
Nature, 263, 663 (1976).
Prostaglandins, 12, 685 (1976).
Prostaglandins, 12, 915 (1976).
Prostaglandins, 12, 375 (1977).
Chemical and Engineering, News, Dec. 20, 17 (1976).
Brit, J. Pharmacol., 76, 423 (1982).
Brit. J. Pharmacol., 84, 595 (1985).
Brit. J. Pharmacol., 86, 643p (1985).
Brit. J. Pharmacol., 102, 251–259 (1991).
Brit. J. Pharmacol., 102, 260–266 (1991).

*Primary Examiner*—C. Warren Ivy
*Assistant Examiner*—Raymond Covington
*Attorney, Agent, or Firm*—Sughrue, Mion, Zinn, Macpeak & Seas

[57] ABSTRACT

A fused benzeneoxyacetic acid derivative of the formula:

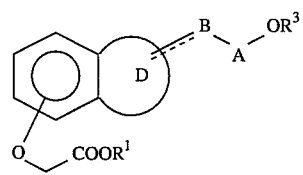

(I)

wherein

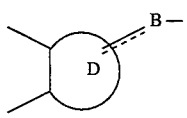

is (i)

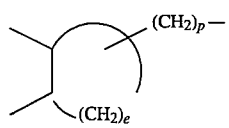

(ii)

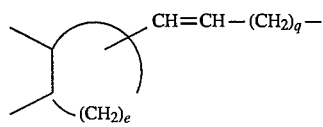

(iii)

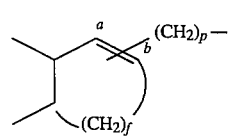

or (iv)

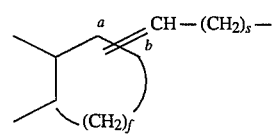

(Abstract continued on next page.)

A is (i)

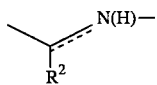

or (ii)

$R^1$ is hydrogen or $C_{1-4}$ alkyl;

$R^2$ is hydrogen, $C_{1-6}$ alkyl or phenyl;

$R^3$ is (i) $C_{1-15}$ alkyl, (ii) $C_{1-8}$ alkyl substituted by one or two of benzene, $C_{4-7}$ cycloalkane or 4–7 ring-membered monocyclic ring which contains one nitrogen atom or (iii) $C_{10-15}$ condensed tricyclic ring;

e is 3–5;

f is 1–3;

p is 0–4;

q is 0–2;

s is 0–3

With the proviso that, ring(s) in $R^3$ may be substituted by one to three of $C_{1-4}$ alkyl, $_{1-4}$ alkoxy, halogen atom, nitro or trihalomethyl. And, when D═B is the formula (iii) or (iv), —(CH2)p- or ═CH—(CH2)s- is attached at the position of a or b on the ring.

and non-toxic salts thereof possess an antagonistic activity on PGI2 receptor, so it is useful for prevention and/or treatment of thrombosis, arteriosclerosis, ischemic heart diseases, gastric ulcer and hypertension.

27 Claims, No Drawings

FUSED BENZENEOXYACETIC ACID DERIVATIVES

SUMMARY

This invention is related to novel fused benzeneoxyacetic acid derivatives.

More particularly, this invention is related to

1) Fused benzeneoxyacetic acid derivatives of the formula:

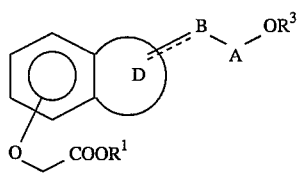

wherein all the symbols are the same meaning as hereafter defined and non-toxic salts thereof, 2) process for the preparation and 3) pharmaceutical agent containing them as active ingredient.

BACKGROUND OF THE INVENTION $PGI_2$ is a natural physiologically active substance having the following structural formula, which is biosynthesized from $PGH_2$ in the metabolic process in vivo called arachidonate cascade.

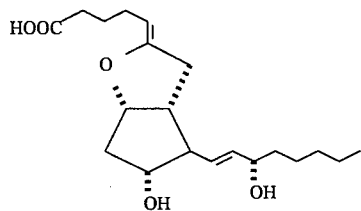

(Nature, 263, 663(1976), Prostaglandins, 12, 685(1976), ibid, 12, 915(1976), ibid, 13, 375(1977) and chemical and Engineering News, Dec. 20, 17(1976))

$PGI_2$ have been confirmed to possess very strong inhibitory action on human blood platelet aggregation and adhesion, inhibitory activity of gastric acid secretion, vasodilatating activity, etc. Therefore it has been considered that $PGI_2$ is useful for prevention and/or treatment for thrombosis, arteriosclerosis, ischemic heart disease, gastric ulcer, hypertension etc. But its application for pharmaceuticals is limited because of its chemical unstableness and difficulty of separation of the actions according to purpose. Accordingly, various $PGI_2$ derivatives were synthesized and many researches have been carried out for keeping of continuity and separation of the actions. But, now we have no satisfied results yet. So, recent research goes to find $PGI_2$ receptor agonist which have non-PG skelton to solve two above problems.

RELATED ARTS

The following compounds are known as compounds which bind $PGI_2$ receptor and have an inhibitory activity on platelet aggregation, i.e. $PGI_2$ agonist in the literature.

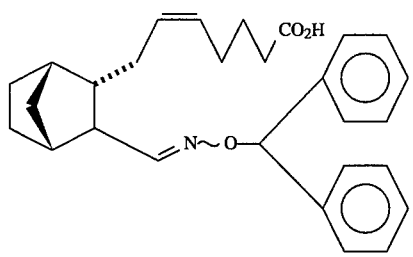

Brit, J. Pharmacol., 76, 423(1982), ibid 84, 595(1985), Brit. J. Pharmacol. Proceedings Supplement, 86, 643P (1985) (1985), and Japanese Kohyo Koho 55-501098.

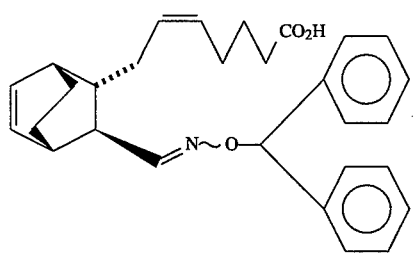

Brit, J, Pharmacol., 76. 423(1982), ibid 84, 595(1985), Brit J. Pharmacol. Proceedings Supplement, 86, 643P (1985); and Japanese Kohyo Koho 57-501127.

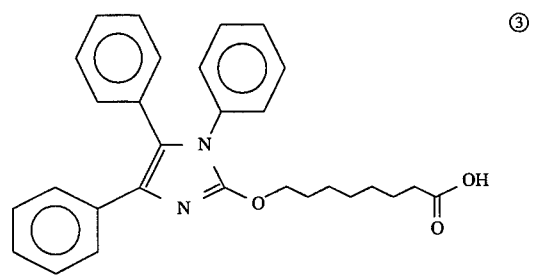

Brit, J, Pharmacol., 102, 251–266(1991), and West German Patent Publication No. 3,504,677.

DISCLOSURE OF THE INVENTION

The present invention is related to

1) A novel fused benzeneoxyacetic acid derivative of the formula:

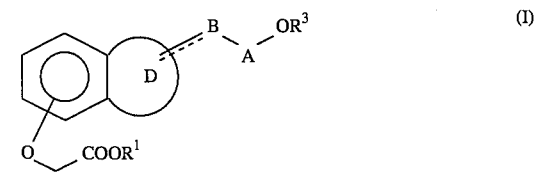

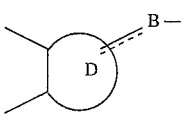

wherein is

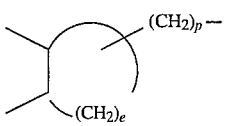

(i)

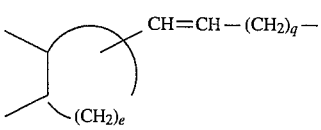

(ii)

or

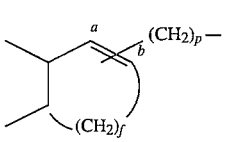

(iii)

or

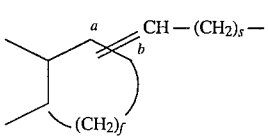

(iv)

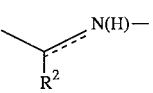

A is
(i)
or

(ii)

$R^1$ is hydrogen or $C_{1-4}$ alkyl;
$R^2$ is hydrogen, $C_{1-6}$ alkyl or phenyl;
$R^3$ is
  (i) $C_{1-15}$ alkyl,
  (ii) $C_{1-8}$ alkyl substituted by one or two of benzene, $C_{4-7}$ cycloalkane, 4–7 ring-membered monocyclic ring which contains one nitrogen atom or
  (iii) $C_{10-15}$ condensed tricyclic ring;
e is 3–5;
f is 1–3;
p is 0–4;
q is 0–2;
s is 0–3.

With the proviso that, ring(s) in $R^3$ may be substituted by one to three of $C_{1-4}$ alkyl, $_{1-4}$ alkoxy, halogen atom, nitro or trihalomethyl. And, when D—B is the formula (iii) or (iv), —(CH2)p- or =CH—(CH2)s- is attached at the position of a or b on the ring.
and non-toxic salts thereof;

2) Process for the preparation of them and

3) Pharmaceutical agent containing them as active ingredient.

Unless otherwise, specified all isomers are included in the invention. For example, alkyl, alkoxy, alkylene and alkenylene includes straight and branched ones. Double bond in alkenylene includes E, Z and EZ mixture. Isomers generated by asymmetric carbon(s) e.g. branched alkyl are included in the invention.

Comparison with the Related Arts

The compounds of the present invention of the formula (I) is novel compounds and it is not easily to predict that such type compounds have an activity of $PGI_2$ receptor agonist.

Salts

The compounds of the present invention of the formula (I), wherein R1 is hydrogen may be converted into the corresponding slats. Non-toxic and water-soluble salts are preferable. Suitable salts, for example are follows: salts of alkaline metal (sodium, potassium etc.), salts of alkaline earth metal (calcium, magnesium etc.), ammonium salts, salts of pharmaceutically-acceptable organic amine salts (fetramethylammonium, triethylamine, methylamine, dimethylamine, cyclopentylamine, benzylamine, phenethylamine, piperidine, monoethanolamine, diethanolamine, tris (hydroxymethyl)amine, lysine, arginine, N-methyl-D-glucamine etc.)

The compounds of the formula (I) or salts thereof may be converted into hydrate by conventional manner.

In the formula (I), $C_{1-4}$ alkyl represented by $R^1$, $R^3$ and substituent(s) in $R^3$ means methyl, ethyl, propyl, butyl and isomeric groups thereof. $C_{1-6}$ alkyl is $R^2$ means methyl, ethyl, propyl, butyl, pentyl, hexyl and isomeric groups thereof.

In the formula (I), $C_{1-15}$ alkyl represented by $R^3$ means methyl, ethyl, propyl, butyl, pentyl, hexyl, heptyl, octyl, nonyl, decyl, undecyl, dodecyl, tridecyl, tetradecyl, pentadecyl and isomeric groups thereof.

In the formula (I), $C_{1-8}$ alkyl represented by $R^3$ means methyl ethyl, propyl, butyl, pentyl, hexyl, heptyl, octyl and isomeric groups thereof.

In the formula (I), $C_{1-4}$ alkoxy as substituent(s) on the ring(s) in $R^3$ means methoxy, ethoxy, propoxy, butoxy and isomeric groups thereof.

In the formula (I), $C_{4-7}$ cycloalkane ring means cyclobutane, cyclopentane, cyclohexane and cycloheptane rings.

In the formula (I), halogen and halogen in trihalomethyl as substituent(s) on the ring(s) in $R^3$ means fluorine, chlorine, bromine and iodine atoms.

In the formula (I), $C_{10-15}$ fused tricyclic ring means indacene, fluerene, anthracene, dibenzocycloheptene rings and partially or fully saturated rings thereof.

Preferable Compounds

In the compounds of the present invention of the formula (I), the following compounds are preferred.

(2-diphenylmethyloxyiminomethyl-1,2,3,4-tetrahydronaphthalen-5-yloxy)acetic acid
[2-(2-diphenylmethyloxyiminoethyl)-1,2,3,4-tetrahydro-naphthalen- 5-yloxy]acetic acid
[1-(2-diphenylmethyloxyiminoethyl)-1,2,3,4-tetrahydro-naphthalen- 5-yloxy]acetic acid
[2-(2-diphenylmethyloxyiminoethyl)-1,2,3,4-tetrahydro-naphthalen- 6-yloxy]acetic acid
[3-(2-diphenylmethyloxyiminoethyl)-1,2,3,4-tetrahydro-naphthalen- 6-yloxy]acetic acid
[2-(3-diphenylmethyloxyiminopropyl)-1,2,3,4-tetrahydro-naphthalen- 5-yloxy]acetic acid
[2-(2-diphenylmethyloxyiminopropyl)-1,2,3,4-tetrahydro-naphthalen- 5-yloxy]acetic acid
[2-[2-(9-fluorenyloxy)iminopropyl]-1,2,3,4-tetrahydro-naphthalen- 5-yloxy]acetic acid
[2-[2-(dibenzo[a,d]cyclohept an-5-yloxy)iminopropyl]- 1,2, 3,4-tetrahydronaphthalen-5-yloxy]acetic a
[2-[2-(dibenzo[a,d]cyclohepten-5-yloxy)iminopropyl]-1,2, 3,4-tetrahydronaphthalen-5-yloxy]acetic acid
[2-[2-bis(4-chlorophenyl)methyloxyiminopropyl]- 1,2,3,4-tetrahydronaphthalen-5-yloxy]acetic acid
[2-[2-bis(4-fluorophenyl)methyloxyiminopropyl]- 1,2,3,4-tetrahydronaphthalen-5-yloxy]acetic acid
[2-[2-[1-phenyl-1-(4-nitrophenyl)methyloxyimino]propyl]-1,2,3,4-tetrahydronaphthalen-5-yloxy]acetic acid
[2-[2-[1-phenyl-1-(4-pyridyl)methyloxyimino]propyl]- 1,2, 3,4tetrahydronaphthalen-5-yloxy]acetic acid
[2-[2-[1-phenyl-1-(3-pyridyl)methyloxyimino]propyl]- 1,2, 3,4tetrahydronaphthalen-5-yloxy]acetic acid
[2-[2-[1-phenyl-1-(2-pyridyl)methyloxyimino]propyl]- 1,2, 3,4-tetrahydronaphthalen-5-yloxy]acetic acid
[2-[2-bis(4-methoxyphenyl)methyloxyiminopropyl]- 1,2,3, 4-tetrahydronaphthalen-5-yloxy]acetic acid
[2-[2-[1-phenyl-1-(4-chlorophenyl)methyloxyimino]propyl]-1,2,3,4-tetrahydronaphthalen-5-yloxy]acetic acid
[2-[2-(phenylmethyloxyiminopropyl)-1,2,3,4-tetrahydro-naphthalen- 5-yloxy]acetic acid
[2-(2-diphenylmethyloxyiminobutyl)-1,2,3,4-tetrahydro-naphthalen- 5-yloxy]acetic acid
[2-(2-diphenylmethyloxyiminopentyl)-1,2,3,4-tetrahydro-naphthalen- 5-yloxy]acetic acid
[2-(2-diphenylmethyloxyimino-3-methylbutyl)-1,2,3,4-tetrahydro-naphthalen- 5-yloxy]acetic acid
[2-(2-diphenylmethyloxyimino-2-phenylethyl)-1,2,3,4-tetrahydro-naphthalen- 5-yloxy]acetic acid
[2-[2-(6-undecyloxyimino)propyl]-1,2,3,4-tetrahydronaphthalen-5-yloxy]acetic acid
[2-[2-(1-phenylhexyloxyimino)propyl]-1,2,3,4-tetrahydronaphthalen- 5-yloxy]acetic acid
[2-[2-(1-phenyl-1-cyclohexylmethyloxyimino)propyl]- 1,2, 3,4tetrahydronaphthalen-5-yloxy]acetic acid
[2-(2-diphenylmethyloxyaminoethyl)-1,2,3,4-tetrahydro-naphthalen- 5-yloxy]acetic acid
[1-(2-diphenylmethyloxyiminoethylidene)-1,2,3,4-tetrahydro-naphthalen- 5-yloxy]acetic acid
[2-(3-diphenylmethyloxyimino-1-propenyl)- 1,2,3,4-tetrahydronaphthalen-5-yloxy]acetic acid
(2-diphenylmethyloxyiminomethyl-3,4-dihydronaphthalen-5yloxy)acetic acid
[1-(2-diphenylmethyloxyaminoethylidene)-1,2,3,4-tetrahydro-naphthalen- 5-yloxy]acetic acid
[2-(3-diphenylmethyloxyamino-1-propenyl)- 1,2,3,4-tetrahydronaphthalen-5-yloxy]acetic acid
[1-(2-diphenylmethyloxyethyl)-1,2,3,4-tetrahydronaphthalen- 5yloxy]acetic acid
(2-diphenylmethyloxyiminomethylbenzocycloheptan-6-yloxy)acetic acid
[1-(2-diphenylmethyloxyiminoethyl)indan-5-yloxy]acetic acid
[1-(2-diphenylmethyloxyiminoethyl)indan-4-yloxy]acetic acid
[2-(2-diphenylmethyloxyiminoethylidene)-1,2,3,4-tetrahydro-naphthalen-5-yloxy]acetic acid
[2-(2-diphenylmethyloxyiminopropylidene)-1,2,3,4-tetrahydro-naphthalen- 5-yloxy]acetic acid
[2-(2-diphenylmethyloxyiminobutylidene)-1,2,3,4-tetrahydro-naphthalen- 5-yloxy]acetic acid
[2-[2-[1-phenyl-1-(4-pyridyl)methyloxyimino]ethylidene]-1,2,3,4-tetrahydronaphthalen-5-yloxy]acetic acid
[2-[2-[1-phenyl-1-(4-pyridyl)methyloxyimino]-propylidene]-1,2,3,4-tetrahydronaphthalen-5-yloxy]acetic acid
[2-[2-[1-phenyl-1-(4-pyridyl)methyloxyimino]butylidene]-1,2,3,4-tetrahydronaphthalen-5-yloxy]acetic acid
[2-(3-diphenylmethyloxyiminopropylidene)-1,2,3,4-tetrahydro-naphthalen- 5-yloxy]acetic acid
[2-(3-diphenylmethyloxyiminobutylidene)-1,2,3,4-tetrahydro-naphthalen- 5-yloxy]acetic acid
[2-(3-diphenylmethyloxyiminopentylidene)-1,2,3,4-tetrahydro-naphthalen- 5-yloxy]acetic acid
[2-[3-[1-phenyl-1-(4-pyridyl)methyloxyimino]propylidene]-1,2,3,4-tetrahydronaphthalen-5-yloxy]acetic acid
[2-[3-[1-phenyl-1-(4-pyridyl)methyloxyimino]butylidene ]-1,2,3,4-tetrahydronaphthalen-5-yloxy]acetic acid
[2-[3-[1-phenyl-1-(4-pyridyl)methyloxyimino ]pentylidene]-1,2,3,4-tetrahydronaphthalen-5-yloxy]acetic acid
[2-(2-diphenylmethyloxyaminoethylidene)-1,2,3,4-tetrahydro-naphthaleno-5-yloxy]acetic acid
[2-(2-diphenylmethyloxyaminopropylidene )-1,2,3,4-tetrahydro-naphthalen- 5-yloxy]acetic acid
[2-(2-diphenylmethyloxyaminobutylidene)-1,2,3,4-tetrahydro-naphthalen- 5-yloxy]acetic acid
[2-[2-[1-phenyl-1-(4-pyridyl)methyloxyamino]ethylidene]-1,2,3,4-tetrahydronaphthalen-5-yloxy]acetic acid
[2-[2-[1-phenyl-1-(4-pyridyl)methyloxyamino]propylidene]-1,2,3,4-tetrahydronaphthalen-5-yloxy]acetic acid
[2-[2-[1-phenyl-1-(4-pyridyl)methyloxyamino]butylidene]-1,2,3,4-tetrahydronaphthalen-5-yloxy]acetic acid
[2-(3-diphenylmethyloxyaminopropylidene)-1,2,3,4-tetrahydro-naphthalen- 5-yloxy]acetic acid
[2-(3-diphenylmethyloxyaminobutylidene)-1,2,3,4-tetrahydro-naphthalen- 5-yloxy]acetic acid
[2-(3-diphenylmethyloxyaminopentylidene)-1,2,3,4-tetrahydro-naphthalen- 5-yloxy]acetic acid
[2-[3-[1-phenyl-1-(4-pyridyl)methyloxyamino]propylidene]-1,2,3,4-tetrahydronaphthalen-5-yloxy]acetic acid
[2-[3-[1-phenyl-1-(4-pyridyl)methyloxyamino]butylidene]-1,2,3,4-tetrahydronaphthalen-5-yloxy]acetic acid
[2-[3-[1-phenyl-1-(4-pyridyl)methyloxyamino]pentylidene]-1,2,3,4-tetrahydronaphthalen-5-yloxy]acetic acid
[2-(2-diphenylmethyloxyiminoethyl)-3,4-dihydro-naphthalen- 5-yloxy]acetic acid
[2-(2-diphenylmethyloxyiminopropyl)-3,4-dihydro-naphthalen- 5-yloxy]acetic acid

[2-(2-diphenylmethyloxyiminobutyl)-3,4-dihydro-naphthalen- 5-yloxy]acetic acid

[2-[2-[1-phenyl-1-(4-pyridyl)methyloxyimino]ethyl]-3,4-dihydronaphthalen-5-yloxy]acetic acid

[2-[2-[1-phenyl-1-(4-pyridyl)methyloxyimino]propyl]- 3,4-dihydronaphthalen-5-yloxy]acetic acid

[2-[2-[1-phenyl-1-(4-pyridyl)methyloxyimino]butyl]- 3,4-dihydronaphthalen-5-yloxy]acetic acid

[2-(3-diphenylmethyloxyiminopropyl)-3,4-dihydronaphthalen- 5-yloxy]acetic acid

[2-(3-diphenylmethyloxyiminobutyl)-3,4-dihydro-naphthalen- 5-yloxy]acetic acid

[2-(3-diphenylmethyloxyiminopentyl)-3,4-dihydro-naphthalen- 5-yloxy]acetic acid

[2-[3-[1-phenyl-1-(4-pyridyl)methyloxyimino]propyl]- 3,4-dihydronaphthalen-5-yloxy]acetic acid

[2-[3-[1-phenyl-1-(4-pyridyl)methyloxyimino]butyl]- 3,4-dihydronaphthalen-5-yloxy]acetic acid

[2-[3-[1-phenyl-1-(4-pyridyl)methyloxyimino]pentyl]- 3,4-dihydronaphthalen-5-yloxy]acetic acid

[2-(2-diphenylmethyloxyaminoethyl)-3,4-dihydronaphthalen- 5-yloxy]acetic acid

[2-(2-diphenylmethyloxyaminopropyl)-3,4-dihydronaphthalen- 5-yloxy]acetic acid

[2-(2-diphenylmethyloxyaminobutyl)-3,4-dihydronaphthalen- 5-yloxy]acetic acid

[2-[2-[1-phenyl-1-(4-pyridyl)methyloxyamino]ethyl]- 3,4-dihydronaphthalen-5-yloxy]acetic acid

[2-[2-[1-phenyl-1-(4-pyridyl)methyloxyamino]propyl]- 3,4-dihydronaphthalen-5-yloxy]acetic acid

[2-[2-[1-phenyl-1-(4-pyridyl)methyloxyamino]butyl]- 3,4dihydronaphthalen-5-yloxy]acetic acid

[2-(3-diphenylmethyloxyaminopropyl)-3,4-dihydronaphthalen- 5-yloxy]acetic acid

[2-(3-diphenylmethyloxyaminobutyl)-3,4-dihydronaphthalen- 5-yloxy]acetic acid

[2-(3-diphenylmethyloxyaminopentyl)-3,4-dihydronaphthalen- 5-yloxy]acetic acid

[2-[3-[1-phenyl-1-(4-pyridyl)methyloxyamino]propyl]- 3,4-dihydronaphthalen-5-yloxy]acetic acid

[2-[3-[1-phenyl-1-(4-pyridyl)methyloxyamino]butyl]- 3,4-dihydronaphthalen-5-yloxy]acetic acid

[2-[3-[1-phenyl-1-(4-pyridyl)methyloxyamino]pentyl]- 3,4-dihydronaphthalen-5-yloxy]acetic acid

[2-(2-diphenylmethyloxyethyl)-1,2,3,4-tetrahydronaphthalen- 5-yloxy]acetic acid

[2-(2-diphenylmethyloxypropyl)-1,2,3,4-tetrahydronaphthalen- 5-yloxy]acetic acid

[2-(2-diphenylmethyloxybutyl)-1,2,3,4-tetrahydronaphthalen- 5-yloxy]acetic acid

[2-[2-[1-phenyl- 1-(4-pyridyl)methyloxy]ethyl]- 1,2,3,4-tetrahydro-naphthaleno5-yloxy]acetic acid

[2-[2-[1-phenyl-1-(4-pyridyl)methyloxy]propyl]- 1,2,3,4-tetrahydronaphthalen-5-yloxy]acetic acid

[2-[2-[1-phenyl-1 -(4-pyridyl)methyloxy]butyl]- 1,2,3,4-tetrahydro-naphthalen-5-yloxy]acetic acid

[2-(3-diphenylmethyloxypropyl)-1,2,3,4-tetrahydronaphthalen- 5-yloxy]acetic acid

[2-(3-diphenylmethyloxybutyl)-1,2,3,4-tetrahydronaphthalen- 5-yloxy]acetic acid

[2-(3-diphenylmethyloxypentyl)-1,2,3,4-tetrahydronaphthalen- 5-yloxy]acetic acid

[2-[3-[1-phenyl-1-(4-pyridyl)methyloxy]propyl]- 1,2,3,4-tetrahydronaphthalen-5-yloxy]acetic acid

[2-[3-[1-phenyl-1-(4-pyridyl)methyloxy]butyl]- 1,2,3,4-tetrahydro-naphthalen-5-yloxy]acetic acid

[2-[3-[1-phenyl-1-(4-pyridyl)methyloxy]pentyl]- 1,2,3,4-tetrahydronaphthalen-5-yloxy]acetic acid

[2-(4-diphenylmethyloxybutyl)-1,2,3,4-tetrahydronaphthalen- 5-yloxy]acetic acid

[2-(4-diphenylmethyloxypentyl)-1,2,3,4-tetrahydronaphthalen- 5-yloxy]acetic acid

[2-(4-diphenyimethyloxyhexyl)-1,2,3,4-tetrahydronaphthalen- 5-yloxy]acetic acid

[2-[4-[1-phenyl-1-(4-pyridyl)methyloxy]butyl]- 1,2,3,4-tetrahydro-naphthalen-5-yloxy]acetic acid

[2-[4-[1-phenyl-1-(4-pyridyl)methyloxy]pentyl]- 1,2,3,4-tetrahydronaphthalen-5-yloxy]acetic acid

[2-[4-[1-phenyl-1-(4-pyridyl)methyloxy]hexyl]- 1,2,3,4-tetrahydronaphthalen-5-yloxy]acetic acid

[2-(3-diphenylmethyloxy-1-propenyl)- 1,2,3,4-tetrahydronaphthalen- 5-yloxy]acetic acid

[2-(3-diphenylmethyloxy-1-butenyl)-1,2,3,4-tetrahydronaphthalen- 5-yloxy]acetic acid

[2-(3-diphenylmethyloxy-1-pentenyl)-1,2,3,4-tetrahydronaphthalen- 5-yloxy]acetic acid

[2-[3-[1-phenyl-1-(4-pyridyl)methyloxy]-1-propenyl]- 1,2,3,4-tetrahydronaphthalen-5-yloxy]acetic acid

[2-[3-[1-phenyl-1-(4-pyridyl)methyloxy]-1-butenyl]- 1,2,3,4-tetrahydronaphthalen-5-yloxy]acetic acid

[2-[3-[1-phenyl-1-(4-pyridyl)methyloxy]-1-pentenyl]- 1,2,3,4-tetrahydronaphthalen-5-yloxy]acetic acid

[2-(4-diphenylmethyloxy-1-butenyl)-1,2,3,4-tetrahydronaphthalen- 5-yloxy]acetic acid

[2-(4-diphenylmethyloxy-1-pentenyl)-1,2,3,4-tetrahydronaphthalen- 5-yloxy]acetic acid

[2-(4-diphenylmethyloxy-1-hexenyl)-1,2,3,4-tetrahydronaphthalen- 5-yloxy]acetic acid

[2-[4-[1-phenyl-1-(4-pyridyl)methyloxy]-1-butenyl]- 1,2,3,4-tetrahydronaphthalen-5-yloxy]acetic acid

[2-[4-[1-phenyl-1-(4-pyridyl)methyloxy]-1-pentenyl]- 1,2,3,4-tetrahydronaphthalen-5-yloxy]acetic acid

[2-[4-[1-phenyl-1-(4-pyridyl)methyloxy]-1-hexenyl]- 1,2,3,4-tetrahydronaphthalen-5-yloxy]acetic acid

[2-[2-[1-phenyl-1-(3-pyrolyl)methyloxyimino]propyl]- 1,2,3,4-tetrahydronaphthalen-5-yloxy]acetic acid

[2-[2-[1-phenyl-1-(3-pyrolyl)methyloxyimino]- 1-propenyl]-1,2,3,4-tetrahydronaphthalen-5-yloxy]acetic acid

[2-[2-[1-phenyl-1-(3-pyrolyl)methyloxyimino]propyl]- 3,4-dihydro-naphthalen-5-yloxy]acetic acid

[2-[2-[1-phenyl-1-(3-pyrolyl)methyloxyimino]propylidene]-1,2,3,4-tetrahydronaphthalen-5-yloxy]acetic acid

[2-[2-[1-phenyl-1-(3-pyrolyl)methyloxy]propyl]- 1,2,3,4-tetrahydronaphthalen-5-yloxy]acetic acid

[2-[2-[1-phenyl-1-(4-azepinyl)methyloxyimino]propyl]- 1,2,3,4-tetrahydronaphthalen-5-yloxy]acetic acid

[2-[2-[1-phenyl-1-(4-azepinyl)methyloxyimino]-1-propenyl]-1,2,3,4-tetrahydronaphthalen-5-yloxy]acetic acid

[2-[2-[1-phenyl-1-(4-azepinyl)methyloxyimino]propyl]- 3,4-dihydro-naphthalen-5-yloxy]acetic acid

[2-[2-[1-phenyl-1-(4-azepinyl)methyloxyimino]propylidene]-1,2,3,4-tetrahydronaphthalen-5-yloxy]acetic acid

[2-[2-[1-phenyl-1-(4-azepinyl)methyloxy]propyl]- 1,2,3,4-tetra-hydronaphthalen-5-yloxy]acetic acid and non-toxic salts thereof and methyl, ethyl esters thereof.

Process for the Preparation

In the compounds of the present invention of the formula (I), compounds wherein $R^1$ is hydrogen, of the formula

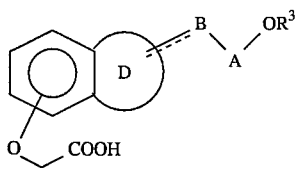 (Ia)

wherein all the symbols are the same meaning as hereinbefore defined.
may be prepared by hydrolysis of a compound of formula

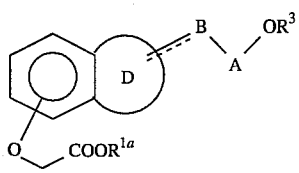 (Ib)

wherein $R^{1a}$ is $C_{1-4}$ alkyl and the other symbols are the same meaning as hereinbefore defined.

Hydrolysis of ester in an alkaline condition is known, for example, it may be carried out in a water-miscible organic solvent (tetrahydrofuran, dioxan, ethanol, methanol, dimethoxyethane or two or more of the mixture etc.), using an alkali (sodium hydroxide, potassium hydroxide etc.), at −10° to 70° C.

In the compounds of formula (Ib), compound wherein A is

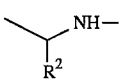

of formula

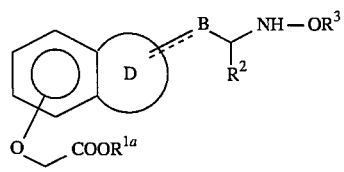 (Ib₁)

wherein all the symbols are the same meaning as hereinbefore defined.
may be prepared by reduction of a compounds of formula (Ib) wherein A is

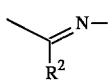

of formula:

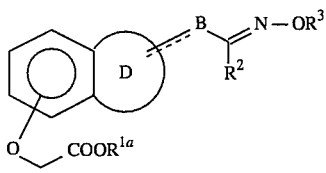 (Ib₂)

wherein all the symbols are the same meaning as hereinbefore defined.

Reduction of imino group into amino group is known reaction, for example, it may be carried out in a water miscible organic solvent (tetrahydrofuran, dioxan, ethanol, methanol, dimethoxyethane or two or more of the mixture etc.), in the presence of acid (hydrochloric acid, acetic acid, trifluoroacetic acid etc.), using reducing agent (sodium cyanoborohydride etc.) at 0° to 70° C.

Compounds of the formula (Ib₂) may be prepared by reacting a compound of formula

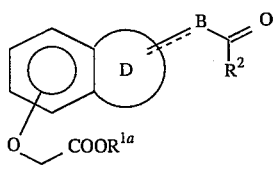 (II)

wherein all the symbols are the same meaning as hereinbefore defined, and a compound of formula $H_2N\text{-}OR^3$ (III)

wherein $R^3$ is the same meaning as hereinbefore defined.

The reaction of ketone and amine is known, for example, it may be carried out in an inert organic solvent (tetrahdyrofuran, methanol, ethanol, dioxan or two or more of the mixture etc.), at 0° to 70° C.

In the formula (Ib), compounds wherein A is

of formula

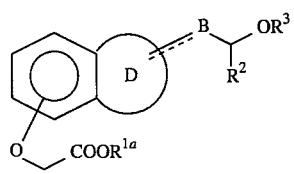 (Ib₃)

wherein all the symbols are the same meaning as hereinbefore defined.
may be prepared by reacting a compound of formula

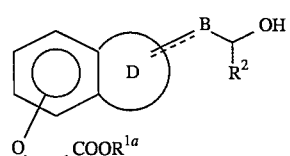 (IV)

wherein all the symbols are the same meaning as hereinbefore defined.

and a compound of formula $$XR^3 \quad (V)$$

wherein X is halogen atom, tosyloxy or mesyloxy group and the other symbols are the same meaning as hereinbefore defined.

The reaction of alcohol and halogenated alkyl is known, for example, it may be carried out in an inert organic solvent (dimethylformamide, dioxan, tetrahydrofuran, dimethoxyethane, acetone or two or more of the mixture etc.), in the presence of a base (potassium t-butoxide, sodium hydride etc.), at −20° to 50° C.

The compounds of the formula (II) and (IV) may be prepared to follow the reaction scheme (A) described in the next page.

Each reaction in the reaction scheme (A) is known per se and each symbol is the following meaning or as defined hereinbefore.

$R^{2a}$: $C_{1-4}$ alkyl or phenyl.

and 10 nM [$^3$H]-iloprost. The membranes were incubated at 24° C. for 30 min. After incubation, 4ml of ice-cold 10 mM Tris-HCl buffer (pH 7.4) was added to the reaction mixture, and filtered through Whatman GF/B glass fiber filter, and washed 4 times with 4 ml of ice-cold 10 mM Tris-HCl buffer (pH 7.4) to separate bound and free [$^3$H]-iloprost. After washing, the filter was dried and radioactivity was counted. Non-specific binding was obtained by performing parallel binding experiments in the presence of 10 μM non-labelled iloprost. Specific binding was calculated by subtracting the non-specific binding from the total binding.

The inhibitory effect of test compound was calculated from the following equation.

The percentage of inhibition (%)=100−($B_1$/$B_0$×100)

$B_1$: specific [$^3$H]-iloprost binding in presence of test compound $B_0$: specific [$^3$H]-iloprost binding in absence of test compound The results are shown in the following table I.

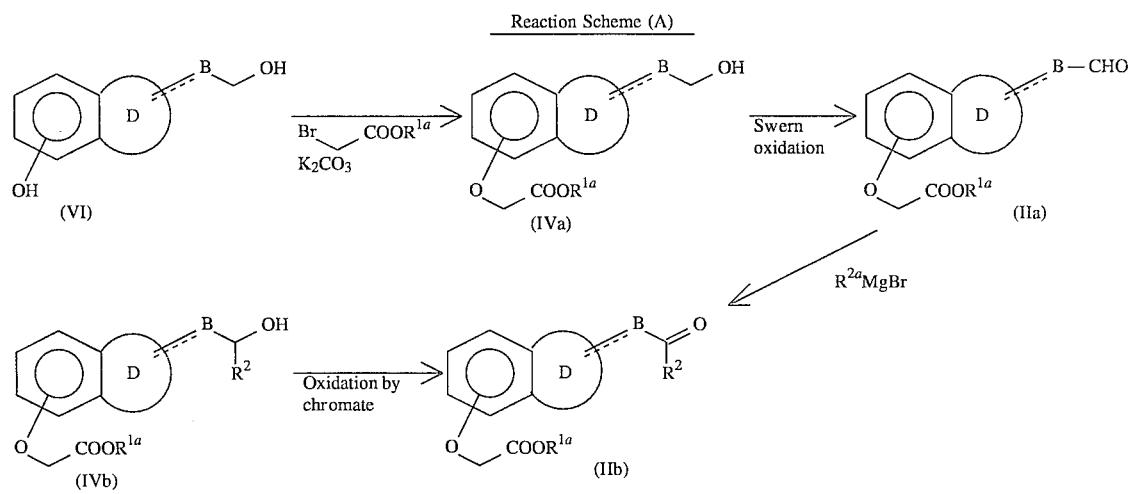

Reaction Scheme (A)

The compounds of the formula (III), (V) and (VI) and reagents are known per se or may be prepared by known methods.

In each reaction in the present specification, products may be purified by conventional manner. For example, it may be carried out by distillation at atmospheric or reduced pressure, high performance liquid chromatography, thin layer chromatography or column chromatography using silica gel or magnesium silicate, washing or recrystallization. Purification may be carried out after each reaction, or after a series of reactions.

Pharmacological Activities

It has been confirmed that the compounds of the present invention of the formula (I) possess an agonistic activity on $PGI_2$ receptor by the following experimental results.

i) Inhibitory activity against $^3$H-iloprost onto $PGI_2$ receptor in human platelet membrane fraction Method of Experiment The binding assay was performed in 200 μl volumes containing 300 μg of platelet plasma membranes. The membranes were added to a buffer composed of 50 mM Tris-HCl (pH 7.4), 15 mM $MgCl_2$, 5 mM EDTA with test compound TABLE i

| Example No. | $IC_{50}$ (μM) |
|---|---|
| 3 | 0.89 |
| 3(a) | 5.4 |
| 3(e) | 3.6 |
| 4 | 2.5 |
| 5 | 7.0 |
| 6 | 0.28 |
| 6(e) | 0.48 |
| 6(f) | 1.0 |
| 6(g) | 0.7 |
| 6(h) | 1.3 |
| 6(i) | 1.8 |
| 6(j) | 1.8 |
| 6(k) | 0.30 |
| 6(l) | 1.4 |
| 6(m) | 0.27 |
| 6(n) | 0.27 |
| 6(o) | 2.3 |
| 6(p) | 2.8 |
| 6(r) | 2.7 |
| 6(s) | 9.6 |
| 8 | 4.0 |
| 9 | 1.9 | ii) Inhibitory effect on Human platelet aggregation Method of experiment

Platelet-rich plasma was prepared from human blood ($5 \times 10^5$ platelets/mm$^3$), and the test compound was added to PRP 1 min prior to the addition of ADP (4 μM). The aggregation was monitored using a platelet aggregometer (NBS HEMA TRACER 601, Niko Bioscience, Japan). The results are shown in the following table II.

TABLE II

| Example No. | IC$_{50}$ (μM) |
| --- | --- |
| 3 | 0.50 |
| 6 | 0.24 |
| 6 (h) | 1.1 |
| 6 (m) | 0.071 |
| 6 (n) | 0.12 |

Toxicity

The toxicity of the compound of the present invention of the formula (I) are very low and are therefore, it may be estimated to be safe for pharmaceutical use.

Application for Pharmaceuticals

The compounds of the present invention of the formula (I) possess an antagonistic activity on PGI$_2$ receptor, so it is expected to be useful for prevention and/or treatment of thrombosis, arteriosclerosis, ischemic heart diseases, gastric ulcer and hypertension.

For the purpose above described, the compounds, of the formula (I), of the present invention and non-toxic salts thereof may be normally by administered systemically or partially usually by oral or parenteral administration.

The doses to be administered are determined depending upon age, body weight, symptom, the desired therapeutic effect, the route of administration, and the duration of the treatment etc. In the human adult, the doses per person per dose are generally between 1 μg and 100 mg, by oral administration, up to several times per day, and between 0.1 μg and 10 mg, by parenteral administration up to several times per day, or contineous administration between 1 and 24 hrs. per day from vein.

As mentioned above, the doses to be used depend upon various conditions. Therefore, there are cases in which doses lower than or greater than the ranges specified above may be used.

When administration of the compounds of the present invention, it is used as solid compositions, liquid compositions or other compositions for oral administration, as injections, liniments or suppositories etc. for parenteral administration.

Solid compositions for oral administration include compressed tablets, pills, capsules, dispersible powders, and granules. Capsules contain hard capsules and soft capsules.

In such compositions, one or more of the active compound(s) is or are, admixed with at least one inert diluent (lactose, mannitol, glucose, hydroxypropyl cellulose, microcrystalline cellulose, starch, polyvinylpyrrolidone, magnesium metasilicate aluminate etc.) The compositions may also comprise, as is normal practice, additional substances other than inert diluents: e.g. lubricating agents (magnesium stearate etc.), disintegrating agents (cellulose calcium glycolate etc.), stabilizing agent (lactose etc.), and assisting agent for dissolving (glutamic acid, asparaginic acid etc.).

The tablets or pills may, if desired, be coated with film of gastric or enteric material (sugar, gelatin, hydroxypropyl cellulose or hydroxypropylmethyl cellulose phthalate etc.), or be coated with more than two films. And further, it may be include capsules of absorbable materials such as gelatin.

Liquid compositions for oral administration include pharmaceutically-acceptable solutions, emulsions, suspensions, syrups and elixirs.

In such compositions, one or more of the active compound(s) is or are comprise in inert diluent(s) commonly used in the art (purified water, ethanol etc.).

Besides inert diluents, such compositions may also comprise adjuvants (wetting agents, suspending agent etc.), sweetening agents, flavouring agents, perfuming agents and preserving agent.

Other compositions for oral administration include spray compositions which may be prepared by known methods and which comprise one or more of the active compound(s).

Spray compositions may comprise additional substances other than inert diluents: e.g. stabilizing agents (sodium sulfite etc.), isotonic buffer (sodium chloride, sodium citrate, citric acid etc.)

For preparation of such spray compositions, for example, the method described in the U.S. Pat. No. 2,868,691 or 3,095,355 may be used.

Injections for parenteral administration include sterile aqueous or non-aqueous solutions, suspensions and emulsions. In such compositions, one more of active compound(s) is or are admixed at least one of inert aqueous diluent(s) (distilled water for injection, physiological salt solution etc.) or inert non-aqueous diluent(s) (propylene glycol, polyethylene glycol, olive oil, ethanol, POLYSOLBATE80 (registered trade mark) etc.).

Injections may comprise aditional other than inert diluents: e.g. preserving agents, wetting agents, emulsifying agents, dispersing agents, stabilizing agent (lactose etc.), assisting agents such as assisting agents for dissolving (glutamic acid, asparaginic acid etc.).

They may be sterilized for example, by filtration through a bacteria-retaining filter, by incorporation of sterilizing agents in the compositions or by irradiation. They also be manufactures in the form of sterile solid compositions, for example, by freeze-drying, and which can be dissolved in sterile water or some other sterile diluents for injection immediately before used.

Other compositions for parenteral administration include liquids for external use, and endermic liniments (ointment etc.), suppositories and pessaries which comprise one or more of the active compound(s) and may be prepared by known methods.

Reference examples and Examples

The following reference examples and examples illustrate the present invention, but not limit the present invention.

Unless otherwise specified, "IR" were measured by KBr tablet method and "NMR" were measured in a solution of CDCl$_3$.

Reference example 1

(2-Hydroxymethyl-1,2,3,4-tetrahydronaphthalen-5-yloxy)acetic acid ethyl ester

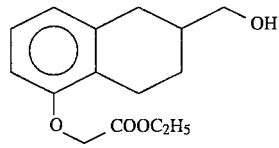

To a stirred suspension of 2-hydroxymethyl-5-hydroxy-1,2,3,4-tetrahydronaphthalene (2.72 g,) and potassium carbonate (3.17 g) in acetonitrile, ethyl bromoacetate (2 ml) was added at room temperature. After stirring overnight at room temperature, the reaction mixture was poured into water and extracted with ether. The extract was washed with saturated brine, dried over magnesium sulfate and evaporated. The residue was purified by silica gel chromatography (hexane:ethyl acetate=6:4) to give the title compound (4.10 g) having the following physical data.

NMR: δ7.05(1H, t), 6.76(1H, d), 6.52(1H, d), 4.82(2H, s), 4.25(2H, q), 3.64(2H, brt), 3.1–2.8(2H,m), 2.7–2.4(2H,m), 2.1–1.8(2H,m), 1.42(1H,m), 1.39 (3H, t).

Reference example 2

(2-Formyl-1,2,3,4-tetrahydronaphthalen-5-yloxy)acetic acid ethyl ester

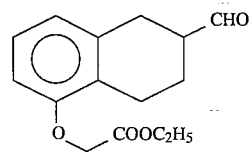

To a stirred solution of oxalyl chloride (1.3 ml) in methylene chloride (30 ml) at −78° C., dimethylsulfoxide (2.26 ml) was added dropwise. Upon complete addition, a solution of the compound prepared in reference example 1 (2.0 g) dissolved in methylene chloride (5 ml) was added dropwise over a 10 min period. Triethylamine (8.5 ml) was added dropwise while the reaction temperature was maintained at −78° C. Upon complete addition, the reaction mixture was warmed slowly to −40° C. over a 20 min period and then quenched by addition of a saturated aqueous solution of ammonium chloride. The organic layer was diluted with ether. The diluted solution was washed several times with a saturated brine and a saturated aqueous solution of ammonium chloride. The organic layer was dried over magnesium sulfate, filtered and evaporated. The residue was filtered through a plug of silica gel (hexane:ethyl acetate= 8:2) to give the title compound (1.89 g) having the following physical data.

TLC: Rf 0.38 (ethyl acetate: n-hexane=1:4)

Reference example 3

[2-(2-Hydroxypropyl)-1,2,3,4-tetrahydronaphthalen-5-yloxy]acetic acid ethyl ester

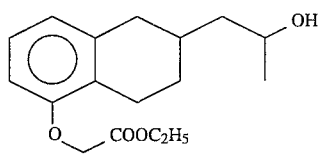

To a stirred solution of the compound prepared in reference example 2 (178 mg) in tetrahydrofuran (10 ml), methyl magnesium bromide (0.645 ml of 1M in tetrahydrofuran) was added dropwise at −50° C. The reaction mixture was warmed −30° C. and stirred for 30 min. After quenching with a saturated aqueous solution of ammonium chloride and the mixture was extracted with ether. The extract was washed with saturated brine, dried over magnesium sulfate and evaporated. The residue was purified by silica gel chromatography (hexane:ethyl acetate=6:4) to give the title compound (116 mg) having the following physical data.

NMR: δ7.03(1H, t), 6.72(1H, d), 6.51(1H,d), 4.61(2H,s), 4.26(2H, q), 4.02(1H, m), 3.1–2.2(4H), 2.1–1.8(2H), 1.7–1.3, 1.30(6H).

Reference example 4

[2-(2-Oxopropyl)-1,2,3,4-tetrahydronaphthalen-5-yloxy]acetic acid ethyl ester

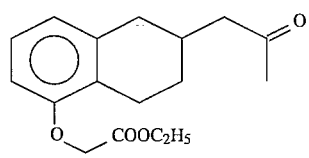

Pyridium dichromate (373 mg) was added to a stirred solution of the compound prepared in reference example 3 (116 mg) in dimethylformamide (4 ml) at room temperature. The mixture was stirred overnight. Celite and florigyl were added to the mixture. The mixture was diluted with a mixture of hexane-ethyl acetate (8:2). The mixture was filtered, the filtrate was evaporated to give the title compound (106 mg).

Reference example 5

1-(2-Hydroxyethylidene)-5-methoxycarbonylmethoxy-1,2,3,4-tetrahydronaphthalene

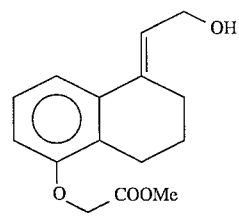

By the same procedure as in reference example 1, using 1-(2-hydroxyethylidene)-5-hydroxy-1,2,3,4-tetrahydronaphthalene (1.5 g), the title compound (1.9 g) was given.

Reference example 5(a)

2-(3-Hydroxy-1-propenyl)-5-methoxycarbonylmethoxy-1,2,3,4-tetrahydronaphthalene

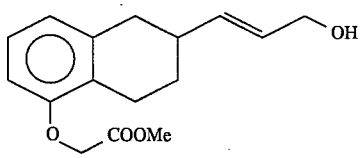

By the same procedure as in reference example 1, using 2-(3-hydroxy-1-propenyl)-5-hydroxy-1,2,3,4-tetrahydronaphthalene (2.5 g), the title compound (3.1 g) was given.

Reference example 5(b)

2-Hydroxymethyl-5-methoxycarbonylmethoxy-3,4-dihydro-naphthalene

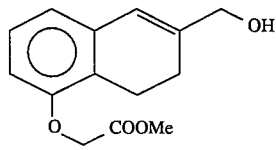

By the same procedure as in reference example 1, using 2-hydroxymethyl- 5-hydroxy-3,4-dihydronaphthalene (2.1 g) the title compound (2.7 g) was given.

Reference example 6

1-Formylmethylidene-5-methoxycarbonylmethoxy-1,2,3,4-tetrahydronaphthalene

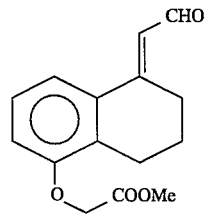

By the same procedure as in reference example 2, using the compound prepared in reference example 5 (800 mg), the title compound (673 mg) was given.

Reference example 6(a)

2-(2-Formylvinyl)-5-methoxycarbonylmethoxy-1,2,3,4-tetrahydronaphthalene

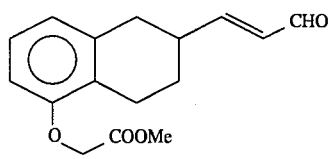

By the same procedure as in reference example 2, using the compound prepared in reference example 5(a) (992 mg), the title compound (840 mg) was given.

Reference example 6(b)

2-Formyl-5-methoxycarbonylmethoxy-3,4-dihydronaphthalene

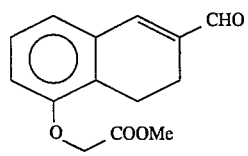

By the same procedure as in reference example 2, using the compound prepared in reference example 5(b) (920 mg), the title compound (710 mg) was given.

EXAMPLE 1

(2-Diphenylmethyloxymethyl-1,2,3,4-tetrahydronaphthalen- 5-yloxy)acetic acid ethyl ester

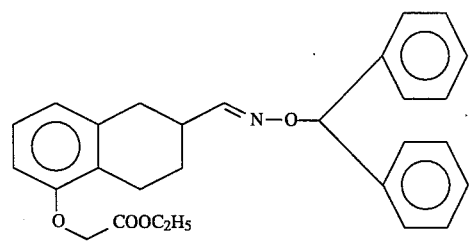

To a stirred solution of the compound prepared in reference example 2 (100 mg) in ethanol (5 ml), benzhydryloxyamine (91 mg) was added at room temperature. After stirring at room temperature overnight, the reaction mixture was evaporated. The residue was purified by silica gel chromatography (8:2 hexane: ethyl acetate=8:2) to give the title compound (160 mg) having the following physical data.

NMR: δ7.59(⅔H, d), 7.3(10H, m), 7.05(1H, t), 6.77(1H, m), 6.65(⅓, d), 6.20(1H, m), 4.65(2H, m), 4.20(2H, q), 3.6–1.0(10H, m). Example 2

(2-Diphenylmethyloxyiminomethyl-1,2,3,4-tetrahydronaphthalen-5-yloxy)acetic acid

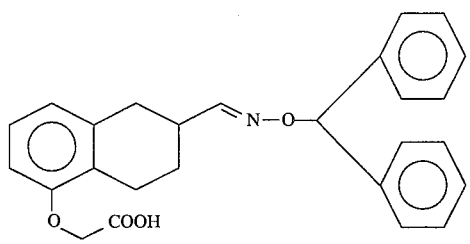

To a stirred solution of the compound prepared in example 1 (160 mg) in dimethoxyethane (3 ml) and methanol (0.5 ml) at room temperature, 1N aqueous solution of sodium hydroxide (0.5 ml) was added. After stirring for 30 min, the reaction mixture was quenched with 1N hydrochloric acid (0.5 ml). The mixture was extracted with ethyl acetate. The extract was washed with water and saturated brine, dried over magnesium sulfate, filtered and evaporated. The residue was purified by silica gel column chromatography (hexane:ethyl acetate=1:1) to give the title compound (118 mg) having the following physical data.

TLC: Rf 0.06 (ethyl acetate);

IR: ν3030, 2932, 1742, 1712, 1604, 1584, 1467, 1454, 1428, 1256, 1120, 1023, 925, 768, 746, 703, 643 $cm^{-1}$.

EXAMPLE 3

[2-(2-Diphenylmethyloxyiminoethyl)-1,2,3,4-tetrahydro-naphthalen-5-yloxy]acetic acid

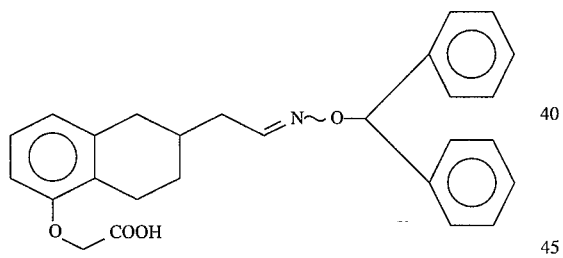

By the same procedure as in reference example 1 and 2 and example 1 and 2, the title compound having the following physical data;

TLC: Rf 0.06 (ethyl acetate);

IR: ν3030, 291 8, 1737, 1709, 1583, 1495, 1467, 1453, 1424, 1253, 1121, 1018, 920, 899, 768 $cm^{-1}$.

EXAMPLE 3(a)–3(e)

By the same procedure as in example 3, using corresponding compound instead of 2-hydroxymethyl-5-hydroxy-1,2,3,4tetrahydronaphthalene, compounds having the following physical data shown in the table III were given.

TABLE III

| Ex. No. | Formula | TLC | IR $_{(cm^{-1})}$ |
|---|---|---|---|
| 3 (a) | | Rf 0.14 (ethyl acetate) | ν 3028, 2936, 1741, 1708, 1582, 1495, 1468, 1454, 1435, 1341, 1304, 1244, 1124, 1005, 902, 780, 743, 700, 607. |

TABLE III-continued

| Ex. No. | Formula | TLC | IR $_{(cm^{-1})}$ |
|---|---|---|---|
| 3 (b) | | Rf 0.14 (ethyl acetate) | ν 3062, 3030, 2942, 1737, 1607, 1588, 1490, 1454, 1434, 1238, 1151, 1096, 1066, 1039, 919, 854, 746, 701. |
| 3 (c) | | Rf 0.14 (ethyl acetate) | ν 3062, 3030, 2917, 1954, 1890, 1733, 1609, 1505, 1455, 1436, 1374, 1231, 1161, 1130, 1080, 1045, 905, 850, 809, 746, 700, 607. |
| 3 (d) | | Rf 0.14 (ethyl acetate) | ν 3062, 3030, 2916, 1954, 1890, 1732, 1610, 1586, 1505, 1454, 1374, 1267, 1163, 1129, 1081, 1046, 929, 832, 746, 699, 607. |
| 3 (e) | | Rf 0.10 (ethyl acetate) | ν 2952, 1738, 1584, 1477, 1455, 1423, 1261, 1115, 1012, 899. |

EXAMPLE 4

[2-(3-Diphenylmethyloxyiminopropyl)-1,2,3,4-tetrahydro-naphthalen- 5-yloxy]acetic acid

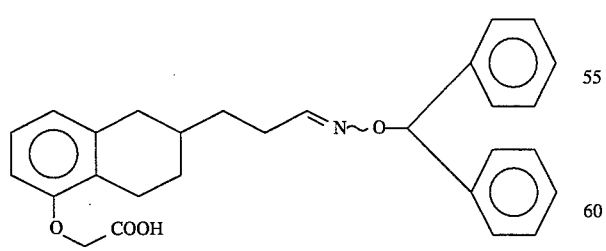

By the same procedure as in reference example 2 and example 1 and 2, the title compound having the following physical data was given.

TLC: Rf 0.06 (ethyl acetate);

IR: ν 3030, 2917, 1738, 1708, 1603, 1583, 1467, 1454, 1427, 1255, 1122, 1015, 924, 768, 746, 699, 603 cm$^{-1}$.

Example 5

[2-(2-Diphenylmethyloxyiminopropyl)-1,2,3,4-tetrahydro-naphthalen- 5-yloxy]acetic acid ethyl ester

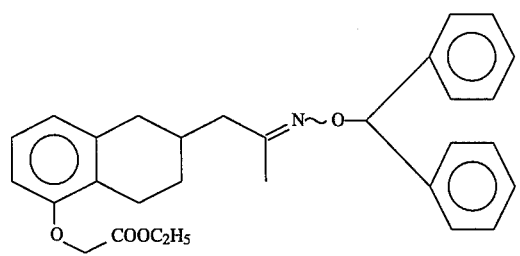

By the same procedure as in example 1, using the compound prepared in reference example 4, the title compound having the following physical data was given.

TLC: Rf 0.52 (n-hexane/ethyl acetate=4: 1);

IR: ν 3030, 2926, 1763, 1730, 1585, 1494, 1466, 1455, 1372, 1241, 1206, 1121, 1043, 937, 766, 745, 702, 611 cm$^{-1}$.

EXAMPLE 6

[2-(2-Diphenylmethyloxyiminopropyl)-1,2,3,4-tetrahydro-naphthalen-5-yloxy]acetic acid

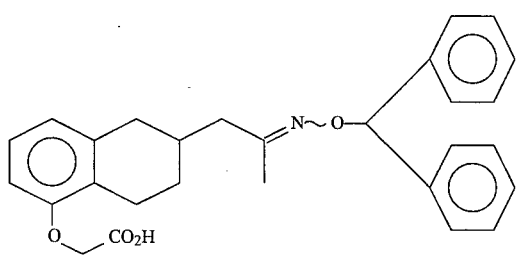

By the same procedure as in example 2, using the compound prepared in example 5, the title compound having the following physical data was given.

TLC: Rf 0.18 (ethyl acetate);

IR: ν 3031, 2926, 1739, 1604, 1585, 1495, 1467, 1455, 1373, 1241, 1120, 1045, 938, 766, 745, 702, 610.cm$^{-1}$.

EXAMPLE 6(a)–6(s)

By the same procedure as in reference example 3 and 4 and example 2, using the compound prepared in reference example 2, the title compounds having the following physical cal data shown in the table IV were given.

With the proviso that, compounds of from example 6(m) to 6(p) were prepared by using corresponding amine, instead of benzhydryloxyamine.

TABLE IV

| Ex. No. | Formula | TLC | IR $_{(cm^{-1})}$ |
|---|---|---|---|
| 6 (a) | | Rf 0.15 (ethyl acetate) | ν 2915, 1737, 1605, 1584, 1466, 1425, 1365, 1258, 1124, 1017, 932, 770, 743. |
| 6 (b) | | Rf 0.19 (ethyl acetate) | ν 3021, 2927, 1736, 1605, 1585, 1466, 1370, 1240, 1119, 1046, 931, 767. |
| 6 (c) | | Rf 0.19 (ethyl acetate) | ν 3015, 2916, 1734, 1585, 1466, 1437, 1372, 1241, 1118, 1048, 933, 799, 768. |

TABLE IV-continued

| Ex. No. | Formula | TLC | IR (cm⁻¹) |
|---|---|---|---|
| 6 (d) | (tetrahydronaphthalene-OCH₂CO₂H)-CH₂-C(CH₃)=N-O-CH(4-Cl-C₆H₄)(3-Cl-C₆H₄) | Rf 0.19 (ethyl acetate) | ν 2917, 1906, 1734, 1585, 1491, 1466, 1436, 1410, 1240, 1090, 1045, 1014, 929, 824, 796, 766. |
| 6 (e) | (tetrahydronaphthalene-OCH₂CO₂H)-CH₂-C(CH₃)=N-O-CH(4-F-C₆H₄)(3-F-C₆H₄) | Rf 0.19 (ethyl acetate) | ν 2929, 1736, 1605, 1585, 1510, 1466, 1224, 1157, 1119, 1015, 929, 834, 767. |
| 6 (f) | (tetrahydronaphthalene-OCH₂CO₂H)-CH₂-C(CH₃)=N-O-CH(C₆H₅)(4-NO₂-C₆H₄) | Rf 0.19 (ethyl acetate) | ν 3033, 2916, 1735, 1606, 1585, 1521, 1466, 1348, 1244, 1109, 1047, 932, 846, 745, 702. |
| 6 (g) | (tetrahydronaphthalene-OCH₂CO₂H)-CH₂-C(CH₃)=N-O-CH(C₆H₅)(3-pyridyl) | Rf 0.13 (ethyl acetate) | ν 3032, 2926, 2477, 1736, 1609, 1589, 1495, 1466, 1417, 1371, 1210, 1117, 1047, 931, 766, 700. |
| 6 (h) | (tetrahydronaphthalene-OCH₂CO₂H)-CH₂-C(CH₃)=N-O-CH(C₆H₅)(3-pyridyl) | Rf 0.13 (ethyl acetate) | ν 3033, 2917, 2472, 1735, 1585, 1466, 1429, 1371, 1239, 1118, 1046, 930, 765, 701. |
| 6 (i) | (tetrahydronaphthalene-OCH₂CO₂H)-CH₂-C(CH₃)=N-O-CH(C₆H₅)(2-pyridyl) | Rf 0.13 (ethyl acetate) | ν 2926, 2508, 1896, 1737, 1601, 1586, 1467, 1436, 1373, 1241, 1118, 1048, 932, 767, 700. |

TABLE IV-continued

| Ex. No. | Formula | TLC | IR $_{(cm^{-1})}$ |
|---|---|---|---|
| 6 (j) | | Rf 0.19 (ethyl acetate) | ν 2929, 2836, 1746, 1611, 1584, 1511, 1467, 1433, 1249, 1173, 1123, 1034, 939, 831, 767, 733. |
| 6 (k) | | Rf 0.19 (ethyl acetate) | ν 2922, 1736, 1585, 1491, 1466, 1436, 1369, 1240, 1120, 1089, 1014, 933, 765, 702. |
| 6 (l) | | Rf 0.27 (methylene chloride:methanol = 9:1) | ν 2933, 1737, 1708, 1583, 1468, 1424, 1368, 1308, 1260, 1125, 1020, 978, 930, 770, 737, 697. |
| 6 (m) | | Rf 0.28 (ethyl acetate:methanol = 10:1) | ν 3700~2000, 1735, 1585, 1495, 1466, 1455, 1240, 1120. |
| 6 (n) | | Rf 0.31 (ethyl acetate:methanol = 10:1) | ν 3700~2000, 1733, 1585, 1466, 1455, 1236, 1120. |
| 6 (o) | | Rf 0.33 (ethyl acetate:methanol = 10:1) | ν 3700~2000, 1739, 1585, 1495, 1466, 1455, 1436, 1245, 1121. |

TABLE IV-continued

| Ex. No. | Formula | TLC | IR (cm⁻¹) |
|---|---|---|---|
| 6 (p) | | Rf 0.29 (ethyl acetate:methanol = 10:1) | ν 3700–2000, 1736, 1585, 1495, 1466, 1452, 1240, 1120. |
| 6 (q) | | Rf 0.20 (ethyl acetate) | ν 2932, 2859, 1747, 1711, 1584, 1466, 1428, 1251, 1123, 935, 763, 735. |
| 6 (r) | | Rf 0.20 (ethyl acetate) | ν 3032, 2927, 1734, 1585, 1466, 1437, 1237, 1120, 1023, 765, 701. |
| 6 (s) | | Rf 0.20 (ethyl acetate) | ν 2925, 2852, 1737, 1585, 1467, 1451, 1245, 1122, 1018, 933, 764, 704. |

EXAMPLE 7

[2-(2-Diphenylmethyloxyaminoethyl)-1,2,3,4-tetrahydronaphthalen-5-yloxy]acetic acid ethyl ester

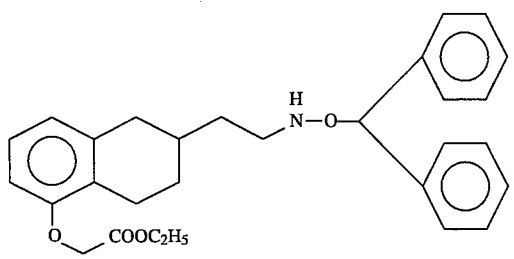

Sodium cyanoborohydride (57 mg) was added to a solution of ethyl ester of the compound prepared in example 3 (140 mg, not yet hydrolized) in a mixture of hydrochloric acid and methanol (pH 3, 4 ml) at room temperature. The mixture was stirred for 1 hr. The mixture was adjusted to neutral by addition of a saturated aqueous solution of sodium bicarbonate. The mixture was extracted with ether. The extract was washed with water and saturated brine, dried over magnesium sulfate and evaporated. The residue was purified by silica gel column chromatography (n-hexane: ethyl acetate=4: 1) to give the title compound having the following physical data.

NMR: δ 7.40–7.20(10H), 7.03(1H, t), 6.70(1H,d), 6.52 (1H,d), 5.72(1H, s), 5.52(1H, s), 4.61 (2H, s), 4.26 (2H, q), 3.10 (2H, t), 2.95 (1H, m), 2.90 (1H, m), 2.60 (1H, m), 2.40 (1H, m), 1.95 (1H, m), 1.75 (1H, m), 1.60 (2H, m), 1.37 (1H, m), 1.30 (3H, t).

EXAMPLE 8

[2-(2-Diphenylmethyloxyaminoethyl)-1,2,3,4-tetrahydro-naphthalen- 5-yloxy]acetic acid

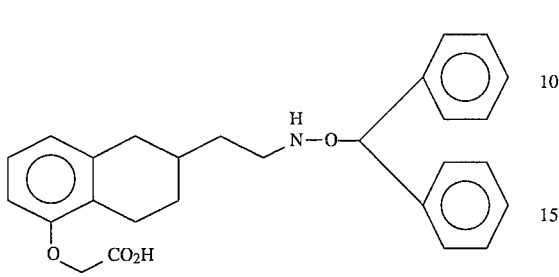

By the same procedure as in example 2, using the compound prepared in example 7, the title compound having the following physical data was given.

TLC: Rf 0.12 (ethyl acetate);

IR: $\nu$ 3032, 2922, 1720, 1630, 1584, 1466, 1411, 1303, 1267, 1219, 1107, 977, 914, 768, 702, 609 $cm^{-1}$.

EXAMPLE 9

(2-Diphenylmethyloxyiminomethyl-pentahydro-benzocycloheptan- 6-yloxy)acetic acid

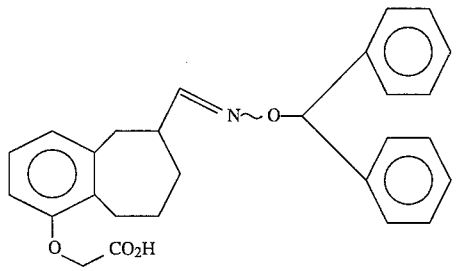

By the same procedure as in reference example 1 and 2 and example 1 and 2, using 2-hydroxymethyl-6-hydroxy-benzocycloheptane, the title compound having the following physical data was given.

TLC: Rf 0.23 (ethyl acetate: methanol=10:1);

IR: $\nu$ 3400, 2921, 1737, 1585 $cm^{-1}$.

EXAMPLE 10

[1-(2-Diphenylmethyloxyiminoethylidene)-1,2,3,4-tetrahydro-naphthalen- 5-yloxy]acetic acid methyl ester

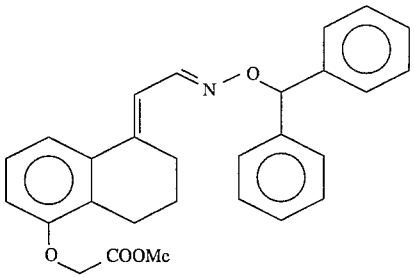

By the same procedure as in example 1, using the compound prepared in reference example 6 (150 mg), the title compound (242 mg) was given.

EXAMPLE 10(a)

[2-(3-Diphenylmethyloxyimino-1-propenyl)-1,2,3,4-tetrahydro-naphthalen-5-yloxy]acetic acid methyl ester

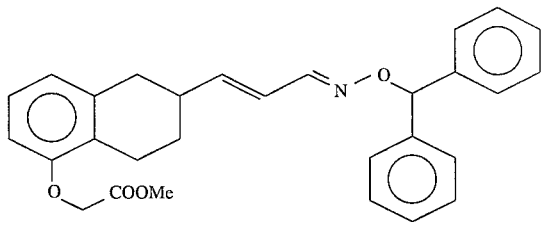

By the same procedure as in example 1, using the compound prepared in reference example 6(a) (150 mg), the title compound (229 mg) was given.

EXAMPLE 10(b)

(2-Diphenylmethyloxyiminomethyl-3,4-dihydro-naphthalen- 5-yloxy)acetic acid methyl ester

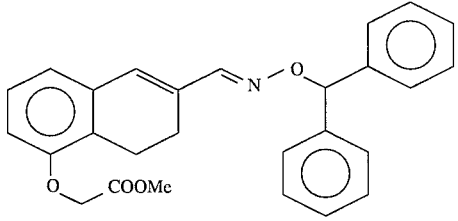

By the same procedure as in example 1, using the compound prepared in reference example 6(b) (144 mg), the title compound (176 mg) having the following physical data was given.

NMR: δ 8.02 (1H, s), 7.4–7.2(10H, m), 7.10(1H, t), 6.78(1H, d), 6.63(1H, d), 6.57(1H, s), 6.28(1H, s), 4.64(2H, s), 3.80(3H, s), 2.88(2H, t), 2.53(2H, t).

EXAMPLE 11

[1-(2-Diphenylmethyloxyaminoethylidene)-1,2,3,4-tetrahydro-naphthalen-5-yloxy]acetic acid methyl ester

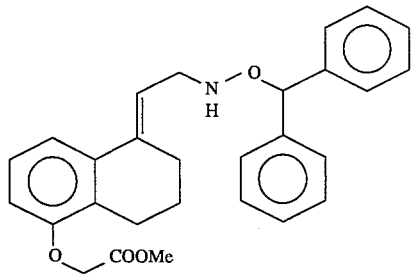

By the same procedure as in example 7, using the compound prepared in example 10 (220 mg), the title compound (177 mg) was given.

EXAMPLE 11(a)

[2-(3-Diphenylmethyloxyamino-1-propenyl)-1,2,3,4-tetrahydro-naphthalen-5-yloxy]acetic acid methyl ester

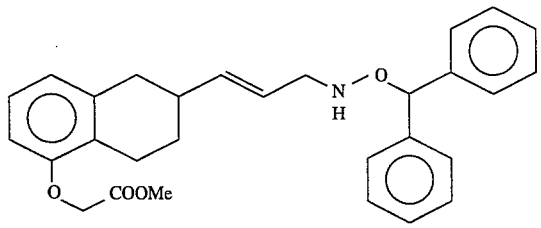

By the same procedure as in example 7, using the compound prepared in example 10(a) (200 mg), the title compound (165 mg) was given.

EXAMPLE 12

[1-(2-Diphenylmethyloxyaminoethylidene)-1,2,3,4-tetrahydro-naphthalen-5-yloxy]acetic acid

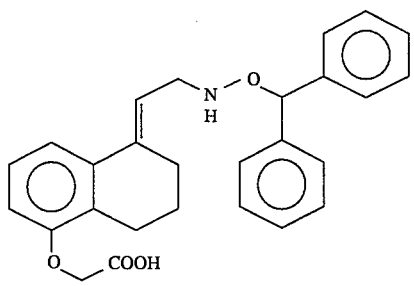

By the same procedure as in example 2, using the compound prepared in example 11 (150 mg), the title compound (115 mg) having the following physical data was given.

NMR: δ 7.40–6.90(12H, m), 6.67(1H, d), 6.15(1H, t), 5.76(1H, s), 4.60(2H, s), 3.62(2H, d), 3.01(1H, m), 2.67(2H, t), 2.43(1H, m), 1.73(2H, m).

EXAMPLE 12(a)

[2-(3-Diphenylmethyloxyamino-1-propenyl)-1,2,3,4-tetrahydro-naphthalen-5-yloxy]acetic acid

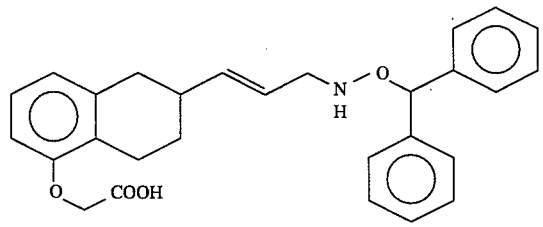

By the same procedure as in example 2, using the compound prepared in example 11(a) (150 mg), the title compound (109 mg) having the following physical data was given.

NMR: δ 7.4–7.2(10H, m), 7.03(1H, t), 6.74(1H, d), 6.53 (1H, d), 5.75(1H, s), 5.70–5.40(2H, m), 4.60(2H, s), 3.55(2H, d), 3.30–1.40(7H, m).

EXAMPLE 12(b)

(2-Diphenylmethyloxyiminomethyl-3,4-dihydro-naphthalen- 5-yloxy)acetic acid

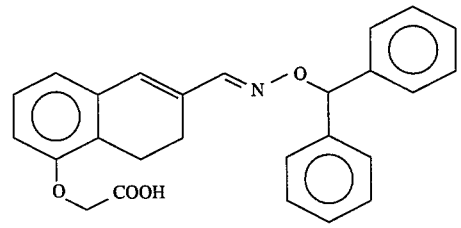

By the same procedure as in example 2, using the compound prepared in example 10(b) (95 mg), the title compound (70 mg) having the following physical data was given.

NMR: δ 8.02(1 H, s), 7.4–7.2(10H, m), 7.12(1 H, t), 6.80(1 H, d), 6.67(1H, d), 6.57(1H, s), 6.28(1H, s), 4.68(2H, s), 2.86(2H, t), 2.53(2H, t).

EXAMPLE 13

[1-(2-Diphenylmethyloxyethyl)-1,2,3,4-tetrahydronaphthalen- 5-yloxy]acetic acid ethyl ester

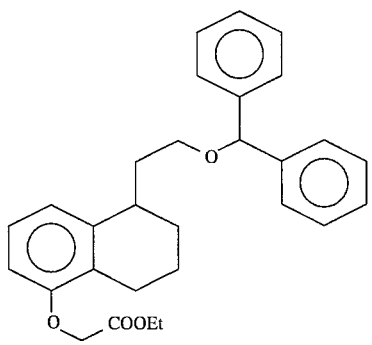

Potassium t-butoxide (810 mg) was added to a solution of [1-(2-hydroxyethyl)- 1,2,3,4-tetrahydronaphthalen-5-yloxy] acetic acid ethyl ester (2.11 g, prepared by the same procedure as in reference example 1) in dimethylformamide (50 ml) at 0° C. The reaction mixture was stirred for 1 hr at room temperature. Benzhydryl bromide (2.15 g) was added to the mixture at 0° C. The mixture was stirred for 1 hr at room temperature. To the mixture, a saturated aqueous solution of ammonium chloride and ether were added. The extract was washed with water and saturated brine, dried over magnesium sulfate and evaporated. The residue was purified by silica gel column chromatography (n-hexane: ethyl acetate= 8: 2) to give the title compound (257 mg).

EXAMPLE 14

[1-(2-Diphenylmethyloxyethyl)-1,2,3,4-tetrahydronaphthalen- 5-yloxy]acetic acid

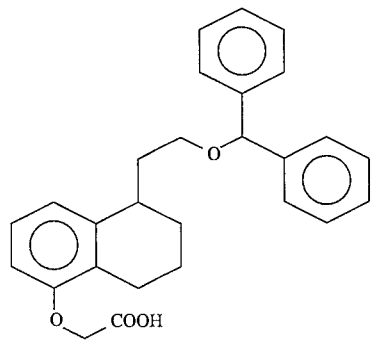

By the same procedure as in example 2, using the compound prepared in example 13 (250 mg), the title compound (160 mg) having the following physical data was given.

TLC: Rf 0.33 (methanol: methylene chloride=1:9)

NMR: δ 7.40–7.20(10H, m), 7.03(1H, t), 6.87(1H, d), 6.55(1H, d), 5.36(1H, s), 4.65(2H, s), 3.05(1H, m), 2.80–2.60(2H, m), 2.07(1H, m), 1.90–1.30(5H, m).

Formulation example 1

The following components were admixed in conventional method and punched out to obtain 100 tablets each containing 5 mg of active ingredient.

| | |
|---|---|
| (2-Diphenylmethyloxyiminomethyl-1,2,3,4-tetrahydronaphthalen-5-yloxy)acetic acid | 500 mg |
| Carboxymethycellulose calcium | 200 mg |
| Magnesium stearate | 100 mg |
| Microcrystalline cellulose | 9.2 g |

While the invention has been described in detail and with reference to specific examples thereof, it will be apparent to one skilled in the art that various changes and modifications can be made therein without departing from the spirit and scope thereof.

What is claimed is:

1. A fused benzeneoxyacetic acid derivative of the formula:

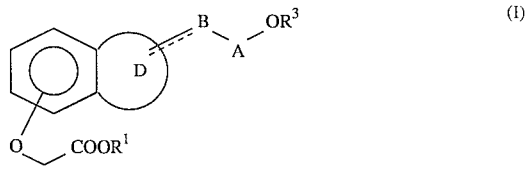

wherein

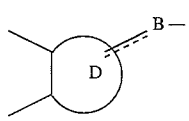

is (i)

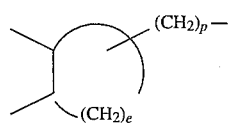

(ii)

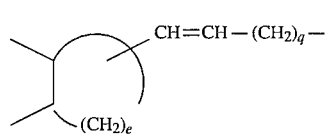

(iii)

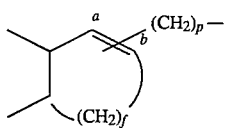

or (iv)

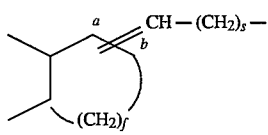

A is (i)

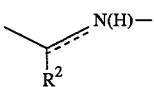

or (ii)

R¹ is hydrogen or $C_{1-4}$ alkyl;
R² is hydrogen, $C_{1-6}$ alkyl or phenyl;
R³ is (i) $C_{1-15}$ alkyl,
  (ii) $C_{1-8}$ alkyl substituted by one or two of benzene, $C_{4-7}$ cycloalkane or 4–7 ring-membered aromatic monocyclic ring which contains one nitrogen atom or
  (iii) $C_{10-15}$ condensed tricyclic ring;
e is 3–5;
f is 1–3;
p is 0–4;
q is 0–2;
s is 0–3;
wherein the ring(s) in R³ may be substituted by one to three substituents selected from the group consisting of $C_{1-4}$ alkyl, $_{1-4}$ alkoxy, halogen atom, nitro and trihalomethyl, and, when D═B is the formula (iii) or (iv), —(CH2)p- or ═CH—(CH2)s- is attached at the position of a or b on the ring; and non-toxic salts thereof.

2. A compound according to claim 1, wherein R³ is $C_{1-8}$ alkyl substituted by one or two of 4–7 ring-membered aromatic monocyclic ring which contains one nitrogen atom or substituted by one of 4–7 ring-membered aromatic monocyclic ring which contains one nitrogen atom and one benzene or $C_{4-7}$ cycloalkane ring.

3. A compound according to claim 2, wherein R³ is $C_{1-8}$ alkyl substituted by one or two of 4 or 5 ring-membered aromatic monocyclic ring which contains one nitrogen atom or substituted by one of 4–7 ring-membered aromatic monocyclic ring which contains one nitrogen atom and one benzene or $C_{4-7}$ cycloalkane ring.

4. A compound according to claim 2, wherein R³ is $C_{1-8}$ alkyl substituted by one or two of 6 ring-membered aromatic monocyclic ring which contains one nitrogen atom or substituted by one of 4–7 ring-membered aromatic monocyclic ring which contains one nitrogen atom and one benzene or $C_{4-7}$ cycloalkane ring.2

5. A compound according to claim 2, wherein R³ is $C_{1-8}$ alkyl substituted by one or two of 7 ring-membered aromatic monocyclic ring which contains one nitrogen atom or substituted by one of 4–7 ring-membered aromatic monocyclic ring which contains one nitrogen atom and one benzene or $C_{4-7}$ cycloalkane ring.

6. A compound according to claim 4, wherein A is

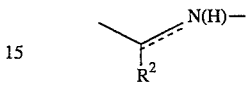

wherein R² is same meaning as defined in claim 1.

7. A compound according to claim 6, wherein e is 4.

8. A compound according to claim 7, wherein said compound is selected from the group consisting of;
[2-[2-[1-phenyl-1-(4-pyridyl)methyloxyimino]propyl]- 1,2,3,4-tetrahydronaphthalen-5-yloxy]acetic acid,
[2-[2-[1-phenyl-1-(3-pyridyl)methyloxyimino]propyl]- 1,2,3,4-tetrahydronaphthalen-5-yloxy]acetic acid,
[2-[2-[1-phenyl-1-(2-pyridyl)methyloxyimino]propyl]- 1,2,3,4-tetrahydronaphthalen-5-yloxy]acetic acid,
and methyl or ethyl esters thereof.

9. A compound according to claim 1, wherein R³ is $C_{1-15}$ alkyl or $C_{1-8}$ alkyl substituted by one or two of benzene or $C_{4-7}$ cycloalkane ring.

10. A compound according to claim 9, A is

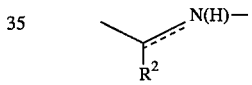

wherein R2 is the same meaning as defined in claim 1.

11. A compound according to claim 10, wherein e is 3.

12. A compound according to claim 11, wherein said compound is selected from the group consisting of;
[1-(2-diphenylmethyloxyiminoethyl)indan-5-yloxy]acetic acid,
[1-(2-diphenylmethyloxyiminoethyl)indan-4-yloxy]acetic acid, and methyl or ethyl esters thereof.

13. A compound according to claim 10, wherein e is 4.

14. A compound according to claim 11, wherein said compound is selected from the group consisting of;
(2-diphenylmethyloxyiminomethyl-1,2,3,4-tetrahydronaphthalen-5-yloxy)acetic acid,
[2-(2-diphenylmethyloxyiminoethyl)- 1,2,3,4-tetrahydronaphthalen-5-yloxy]acetic acid,
[1-(2-diphenylmethyloxyiminoethyl)- 1,2,3,4-tetrahydronaphthalen-5-yloxy]acetic acid,
[2-(2-diphenylmethyloxyiminoethyl)- 1,2,3,4-tetrahydronaphthalen-6-yloxy]acetic acid,
[3-(2-diphenylmethyloxyiminoethyl)- 1,2,3,4-tetrahydronaphthalen-6-yloxy]acetic acid,
[2-(3-diphenylmethyloxyiminopropyl)- 1,2,3,4-tetrahydronaphthalen-5-yloxy]acetic acid,
[2-(2-diphenylmethyloxyiminopropyl)- 1,2,3,4-tetrahydronaphthalen-5-yloxy]acetic acid,
[2-[2-bis(4-chlorophenyl)methyloxyiminopropyl]- 1,2,3,4-tetrahydronaphthalen-5-yloxy]acetic acid,
[2-[2-bis(4-fluorophenyl)methyloxyiminopropyl]- 1,2,3,4-tetrahydronaphthalen-5-yloxy]acetic acid,

[2-[2-[1-phenyl-1-(4-nitrophenyl)methyloxyimino]propyl]-1,2,3,4-tetrahydronaphthalen-5-yloxy]acetic acid,
[2-[2-bis(4-methoxyphenyl)methyloxyiminopropyl]- 1,2,3,4-tetrahydronaphthalen-5-yloxy]acetic acid,
[2-[2-[1-phenyl-1-(4-chlorophenyl)methyloxyimino]propyl]-1,2,3,4-tetrahydronaphthalen-5-yloxy]acetic acid,
[2-[2-(phenylmethyloxyiminopropyl)- 1,2,3,4-tetrahydronaphthalen-5-yloxy]acetic acid,
[2-(2-diphenylmethyloxyiminobutyl)- 1,2,3,4-tetrahydronaphthalen-5-yloxy]acetic acid,
[2-(2-diphenylmethyloxyiminopentyl)- 1,2,3,4-tetrahydronaphthalen-5-yloxy]acetic acid,
[2-(2-diphenylmethyloxyimino-3-methylbutyl)- 1,2,3,4-tetrahydro-naphthalen-5-yloxy]acetic acid,
[2-(2-diphenylmethyloxyimino-2-phenylethyl)- 1,2,3,4-tetrahydro-naphthalen-5-yloxy]acetic acid,
[2-[2-(6-undecyloxyimino)propyl]- 1,2,3,4-tetrahydronaphthalen-5yloxy]acetic acid,
[2-[2-(1-phenylhexyloxyimino)propyl]- 1,2,3,4-tetrahydronaphthalen-5-yloxy]acetic acid,
[2-[2-(1-phenyl-1-cyclohexylmethyloxyimino)propyl]- 1,2,3,4-tetrahydronaphthalen-5-yloxy]acetic acid,
[2-(2-diphenylmethyloxyaminoethyl)- 1,2,3,4-tetrahydronaphthalen-5-yloxy]acetic acid,
[2-(3-diphenylmethyloxyimino-1-propenyl)- 1,2,3,4-tetrahydronaphthalen-5-yloxy]acetic acid,
[2-[2-(3-diphenylmethyloxyamino)-1-propenyl]- 1,2,3,4-tetrahydronaphthalen-5-yloxy]acetic acid, and methyl or ethyl esters thereof.

15. A compound according to claim 10, wherein e is 5.
16. A compound according to claim 15, wherein said compound is selected from the group consisting of;
(2-diphenylmethyloxyiminomethylbenzocycloheptan-6-yloxy)acetic acid
or methyl or ethyl esters thereof.
17. A compound according to claim 10, wherein f is 2.
18. A compound according to claim 17, wherein said compound is selected from the group consisting of;
[1-(2-diphenylmethyloxyiminoethylidene)- 1,2,3,4-tetrahydro-naphthalen-5-yloxy]acetic acid,
(2-diphenylmethyloxyiminomethyl-3,4-dihydronaphthalen-5yloxy)acetic acid,
[1-(2-diphenylmethyloxyaminoethylidene)- 1,2,3,4-tetrahydro-naphthalen-5-yloxy]acetic acid,
and methyl or ethyl esters thereof.

19. A compound according to claim 9, wherein A is

wherein R2 is the same meaning as defined in claim 1.
20. A compound according to claim 19, wherein e is 4.
21. A compound according to claim 20, wherein said compound is selected from the group consisting of;
[1-(2-diphenylmethyloxyethyl)- 1,2,3,4-tetrahydronaphthalen-5-yloxy]acetic acid
methyl or ethyl esters thereof.
22. A compound according to claim 1, wherein $R^3$ is $C_{10-15}$ condensed tricyclic ring.
23. A compound according to claim 22, wherein A is

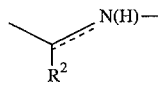

wherein R2 is the same meaning as defined in claim 1.
24. A compound according to claim 23, wherein e is 4.
25. A compound according to claim 24, wherein said compound is selected from the group consisting of;
[2-[2-(9-fluorenyloxy)iminopropyl]- 1,2,3,4-tetrahydronaphthalen-5-yloxy]acetic acid,
[2-[2-(dibenzo[a,d]cycloheptan-5-yloxy)iminopropyl]- 1,2,3,4-tetrahydronaphthalen-5-yloxy]acetic acid,
[2-[2-(dibenzo[a,d]cyclohepten-5-yloxy)iminopropyl]- 1,2,3,4-tetrahydronaphthalen-5-yloxy]acetic acid,
and methyl or ethyl esters thereof.
26. A composition for treating thrombosis, arteriosclerosis, ischemic heart diseases, gastric ulcer or hypertension, comprising;
(a) a pharmaceutically effective amount of a fused benzeneoxyacetic acid derivative of the formula (I) of claim 1, and
(b) a pharmaceutically acceptable carrier and/or coating.
27. A method for treating thrombosis, arteriosclerosis, ischemic heart diseases, gastric ulcer or hypertension, comprising administering to a subject a pharmaceutically effective amount of a fused benzeneoxyacetic acid derivative of the formula (I) of claim 1.

* * * * *